US00PP24522P3

(12) United States Plant Patent
Madsen

(10) Patent No.: US PP24,522 P3
(45) Date of Patent: Jun. 3, 2014

(54) *CAMPANULA* PLANT NAMED 'PKMTAK3'

(50) Latin Name: *Campanula takesimana*
Varietal Denomination: PKMTAK3

(75) Inventor: Christian Hald Madsen, Korsor (DK)

(73) Assignee: Gartneriet PKM A/S, Odense N (DK)

( * ) Notice: Subject to any disclaimer, the term of this patent is extended or adjusted under 35 U.S.C. 154(b) by 79 days.

(21) Appl. No.: 13/507,740

(22) Filed: Jul. 25, 2012

(65) Prior Publication Data

US 2014/0033386 P1 Jan. 30, 2014

(51) Int. Cl.
*A01H 5/00* (2006.01)

(52) U.S. Cl.
USPC ..... Plt./414

(58) Field of Classification Search
USPC ..... Plt./414
See application file for complete search history.

*Primary Examiner* — Susan McCormick Ewoldt
(74) *Attorney, Agent, or Firm* — Foley & Lardner LLP

(57) ABSTRACT

A new and distinct cultivar of *Campanula* plant named 'PKMTAK3', characterized by its compact plant habit; dense and bushy plant form; vigorous growth habit; and large, purple flowers.

10 Drawing Sheets

Latin name of genus and species of the plant claimed: *Campanula takesimana.*

Variety denomination: 'PKMTAK3'.

BACKGROUND OF THE INVENTION

The present invention relates to a new and distinct cultivar of *Campanula* plant, botanically known as *Campanula takesimana*, commonly known as Bellflower, and hereinafter referred to by the name 'PKMTAK3'.

The new *Campanula*, 'PKMTAK3', is a product of a planned breeding program conducted by the inventor, Christian Hald Madsen, in Søhus, Denmark. The new *Campanula* originated from a cross made by the inventor in March 2009 between a proprietary selection of *Campanula takesimana* designated 21.01.0083 (breeder reference, unpatented) as the female parent and a proprietary selection of *Campanula punctata* designated 39.00.3010 (breeder reference, unpatented) as the male parent. The new *Campanula* 'PKMTAK3' was discovered and selected by the inventor as a single flowering plant within the progeny of the stated cross in a controlled environment in Søhus, Denmark. The inventor selected 'PKMTAK3' on the basis of its compact plant habit and purple flowers.

Asexual reproduction of the new *Campanula* cultivar by terminal cuttings has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMTAK3'. These characteristics in combination distinguish 'PKMTAK3' as a new and distinct cultivar:

1. Compact plant habit;
2. Dense and bushy plant form, mainly due to short, upright and stiff stems;
3. Strong peduncles in greyed-purple and green color;
4. Purple and white flowers.

Plants of the cultivar 'PKMTAK3' can be compared to the *Campanula takesimana* cultivar 'PKMTAK2' (U.S. plant patent application Ser. No. 13/507,208). In side-by-side comparisons conducted by the inventor in Stige, Denmark, plants of the instant cultivar 'PKMTAK3' and plants of the cultivar 'PKMTAK2' differ in the following characteristics:

1. Plants of the 'PKMTAK3' produce flowers with a deep purple color whereas plants of 'PKMTAK2' produce light red-purple flowers.
2. Plants of 'PKMTAK3' have greyed-purple peduncles whereas plants of 'PKMTAK2' have green peduncles.

BRIEF DESCRIPTION OF THE PHOTOGRAPHS

The accompanying colored photographs illustrate the overall appearance of the new *Campanula* 'PKMTAK3', showing the colors as true as it is reasonably possible to obtain in colored reproductions of this type. Colors in the photographs may differ slightly from the color values cited in the detailed botanical description, which more accurately describe the actual colors of 'PKMTAK3'.

Figure 1:
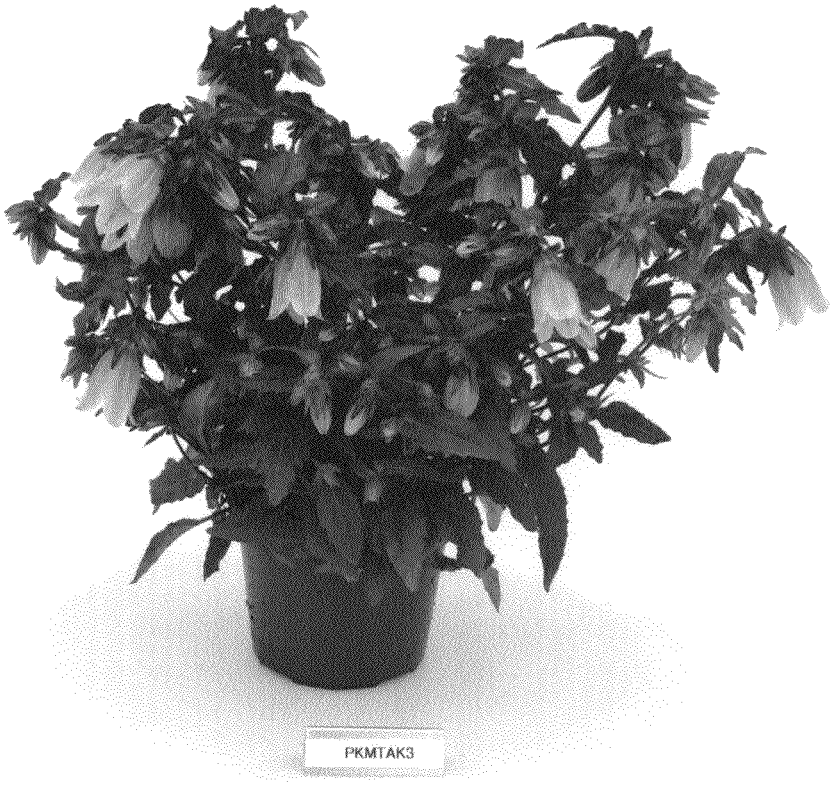

FIG. 1 comprises a side perspective view of a typical flowering plant of PKMTAK3.

Figure 2:
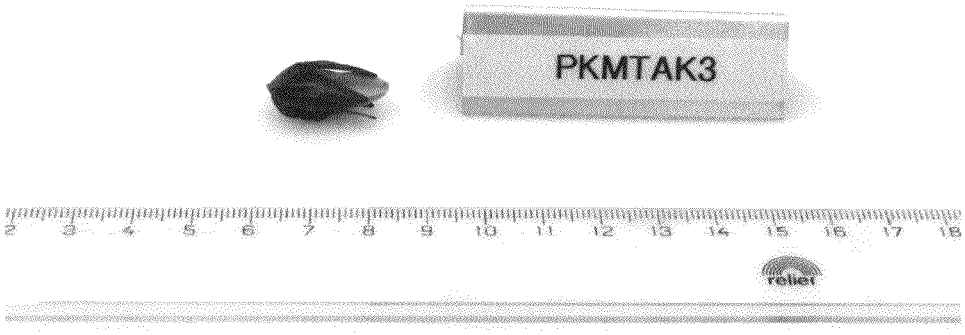

FIG. 2 comprises a close-up side perspective view of a typical young bud of PKMTAK3.

Figure 3:
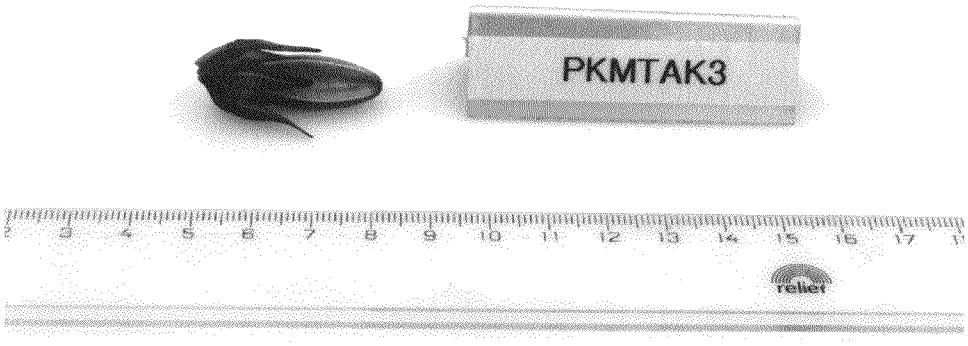

FIG. 3 comprises a close-up side perspective view of a typical mature bud of PKMTAK3.

Figure 4:
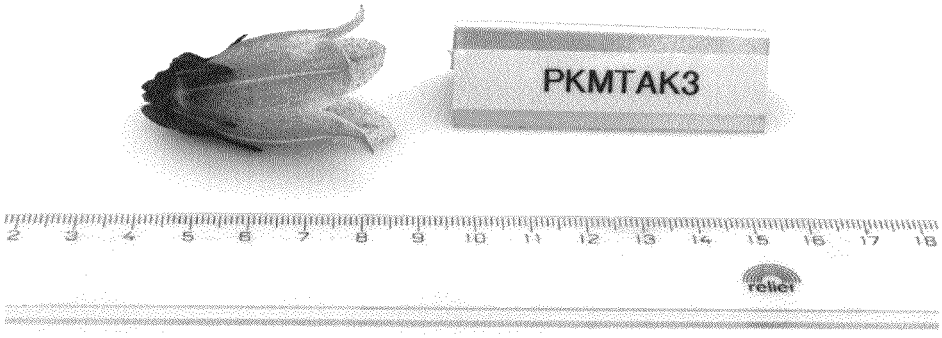

FIG. 4 comprises a close-up side perspective view of a typical flower of PKMTAK3.

Figure 5:
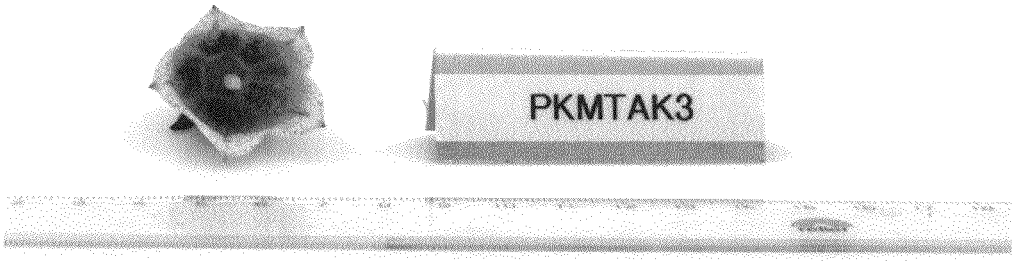

FIG. 5 comprises a close-up front perspective view of a typical flower of PKMTAK3.

Figure 6:
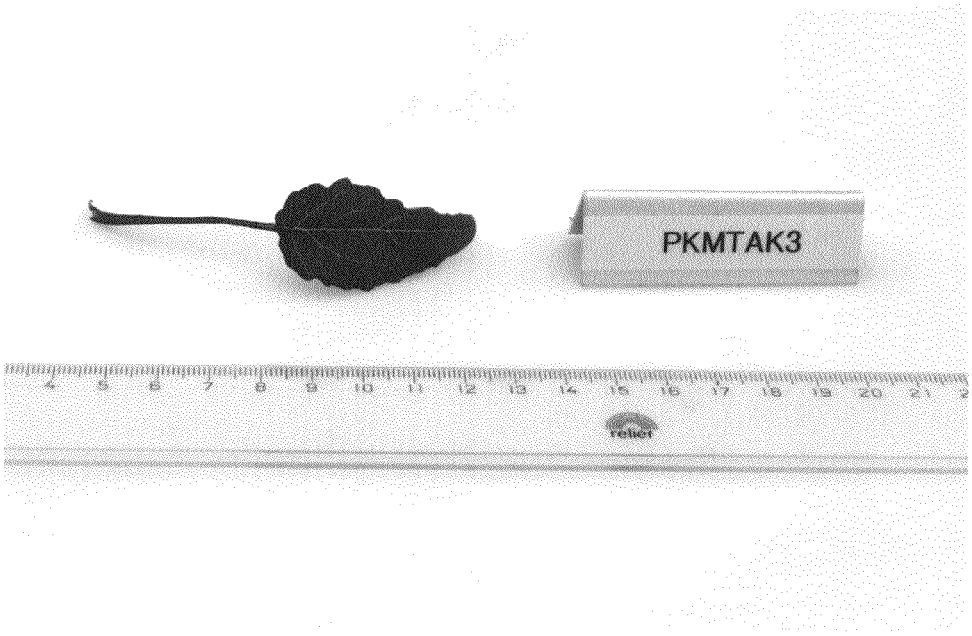

FIG. 6 comprises a close-up side perspective view of a typical basal leaf of PKMTAK3.

Figure 7:
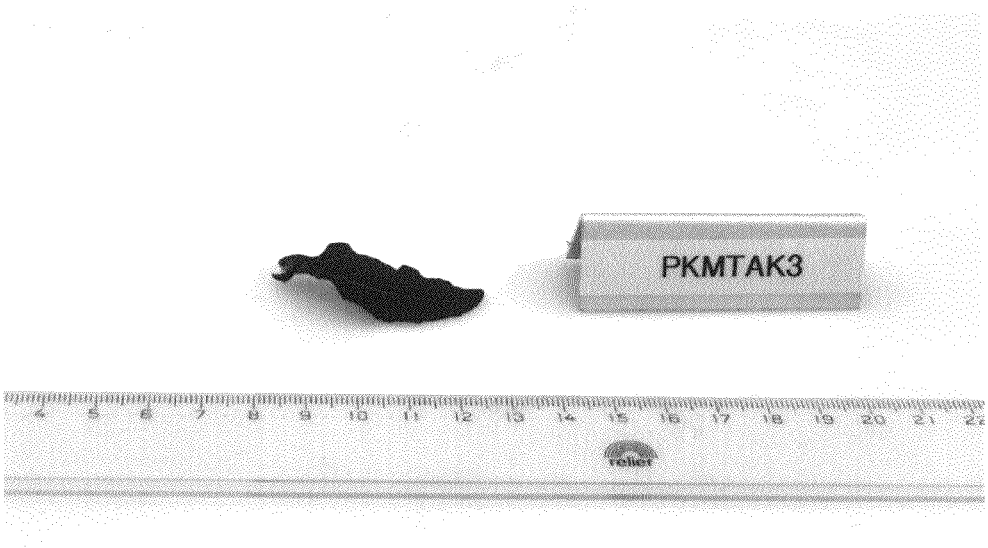

FIG. 7 comprises a close-up side perspective view of a typical apical leaf of PKMTAK3.

Figure 8:
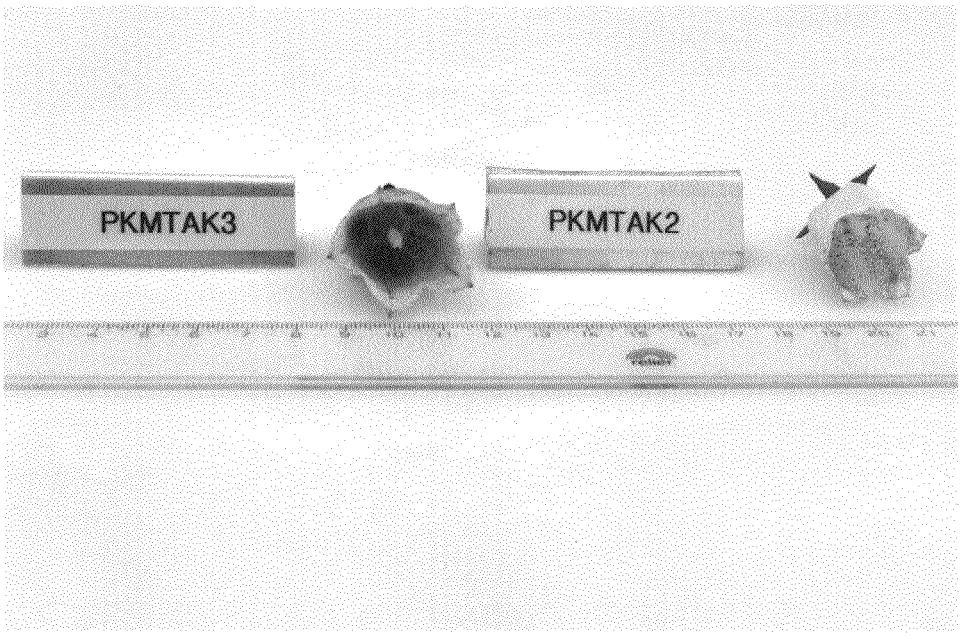

FIG. 8 comprises a close-up front perspective view of a typical flower of 'PKMTAK2' compared with a typical flower of 'PKMTAK3'

Figure 9:
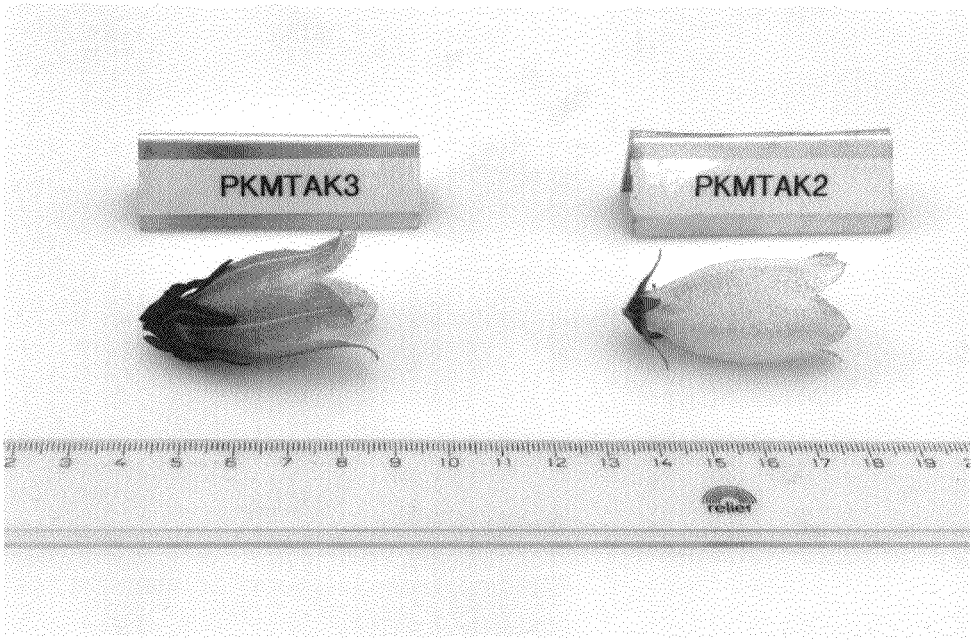

FIG. 9 comprises a close-up side perspective view of a typical flower of 'PKMTAK2' compared with a typical flower of 'PKMTAK3'

Figure 10:
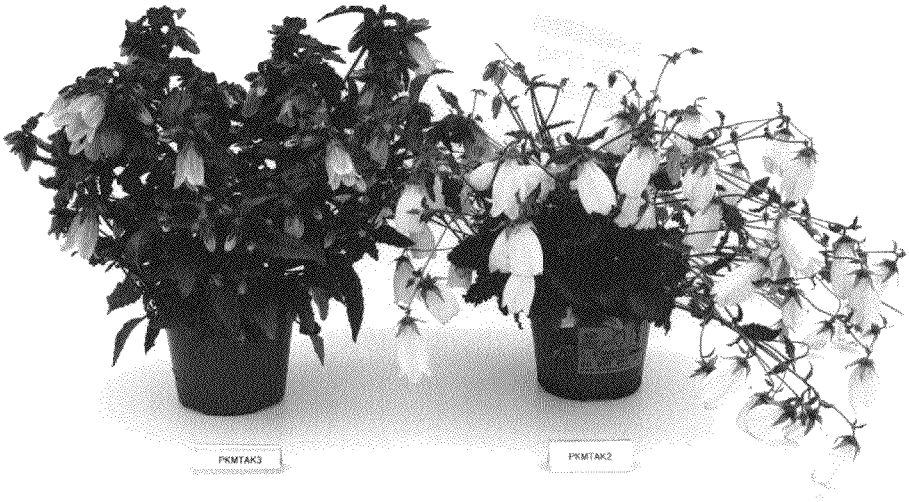

FIG. 10 comprises a side perspective view of a typical flowering plant of PKMTAK3 compared with a typical flowering plant of PKMTAK2.

DETAILED BOTANICAL DESCRIPTION

The new *Campanula* 'PKMTAK3' has not been observed under all possible environmental conditions. The phenotype of the new cultivar may vary with variations in environment such as temperature, light intensity, day length, and fertility level without any variance in genotype.

The aforementioned photographs, together with the following observations, measurements and values describe plants of the new *Campanula* 'PKMTAK3' as grown under greenhouse conditions. No growth retardants were used.

The age of the 'PKMTAK3' plants described is about 10 months after cutting. Color references are made to The Royal Horticultural Society Colour Chart (R.H.S.), $5^{th}$ edition, except where general colors of ordinary significance are used.

Classification:

*Botanical.*—*Campanula takesimana.*

Parentage:

*Female or seed parent.*—*Campanula takesimana* designated 21.01.0083 (breeder reference, unpatented).

*Male or pollen parent.*—*Campanula punctata* designated 39.00.3010 (breeder reference, unpatented).

Propagation:

*Type cutting.*—Terminal vegetative cuttings.

*Time to initiate roots.*—About 12 to 15 days at 18 to 21° C. in tunnels in a greenhouse.

*Root description.*—Fine, well branched.

Plant description:

*Form.*—Perennial, herbaceous plant with upright, compact plant habit. Produced as potted plant. Campanulate flowers in racemes. Freely branching from rhizomes.

*Crop time.*—After rooting, about 9-11 months are required to produce finished flowering plants in 10.5 cm pots.

*Plant height* (*from pot rim to top of plant plane*).—20-25 cm from pot rim.

*Plant spread* (*width*).—32 to 38 cm.

*Lateral branches.*—Quantity: 15 to 20 per plant. Length (including flowers): 10-30 cm. Diameter: 1 to 3 mm. Internode Length: 15-40 mm.

*Stem.*—Shape: Square. Strength: Stiff. Aspect: Upright, slightly bending when bearing flowers. Pubescence: very short hairs, hispidulous. Upper parts glabrous. Color: RHS 166A, greyed-orange; some young stems RHS 138A green.

Foliage description:

*Arrangement.*—Alternate, heterophyllous.

*Basal leaves.*—Arrangement: Single. Overall shape: Ovate. Apex shape: Acute. Base shape: Cordate. Length: 30-85 mm. Width: 20-30 mm. Margin: Crenate. Texture (both sides): Grooved.

*Apical* (*stem*) *leaves.*—Overall shape: Lanceolate. Apex shape: Acute. Base shape: Cordate, sessile. Length: About 30-70 mm. Width: About 12-20 mm. Margin: Serrate. Texture (both sides): Grooved.

*Pubescence.*—None.

*Basal & apical leaf color.*—Mature: Upper surface: Green, RHS N137A. Lower Surface: Green, RHS 138A. Some apical leaf margins RHS 187A, greyed-purple. Immature: Upper surface: Green, RHS 137A. Lower Surface: Green, RHS 138A. Some apical leaf margins RHS 187A grayed-purple. Venation: Pattern: Reticulate. Color: Upper Surface: Green, RHS 137A. Lower Surface: Green, RHS 138A. Petiole: Arrangement: Angular. Basal Length: 2-4 cm. Apical Length: 0 cm. Diameter: 1-5 mm. Color: RHS 137A, green; some RHS 187A greyed-purple.

Inflorescence description:

*Flower arrangement and shape.*—Single, large, campanulate flowers in racemes, drooping, acropetal flowering habit.

*Natural flowering season.*—May to July.

*Time to flower.*—About 8 weeks after planting of rooted cutting.

*Flower longevity.*—Longevity of individual flowers is highly dependent on temperature and light conditions. Flowers persistent.

*Inflorescence size.*—Height: 5 to 10 cm. Diameter: 50-70 mm.

*Number of flowers per inflorescence.*—3 to 5.

*Flowers.*—Arrangement and shape: Campanulate, acropetal, drooping. Flowers single, sympetalous, campanulate, somewhat gibbous. Height: 30-40 mm. Diameter: 20-30 mm.

*Buds.*—Length: Up to 25 mm. Diameter: Up to 10 mm. Shape: Oblong, ridged, fluted. Color: Young buds: RHS N149D yellow-green. Mature buds: Ridges: RHS N77B purple; blotchy. Valleys: RHS 149D, yellow-green.

*Petals.*—Appearance: Shiny, single, sympetalous, sympetalous, somewhat gibbous. Quantity per flower: 5. Length: 10 mm. Width: Base of lobe 10 mm. Overall Shape: Lobes triangular. Tip: Acute. Base: Fused. Margin: Entire. Texture: Outside bell: Glabrous. Inside bell: hispidulous.

*Color* (*when opening*).—Outside bell: Ground color RHS N155D white, base RHS N77B purple changing to N155D white at tip. Inside bell: Ground color RHS N155D, white; few dots RHS 77B purple.

*Color* (*fully opened*).—Outside bell: Ground color RHS N155D white, base RHS N77B purple changing to N155D white at tip. Inside bell: Ground color RHS N155D, white; many dots RHS 77B purple. Fading: No fading; withers to RHS N92A violet-blue.

*Sepals.*—Arrangement: Shiny and free. Quantity per flower: 5. Length: 20 mm. Width: 5 mm. Overall shape: Hastate, sessile, clasping. Apex: Acute. Base: Sessile. Margin: Entire. Texture: Glabrous. Color (immature): Upper and lower surfaces: Green, RHS 138A. Color (mature) Upper surface: RHS 138A green; some tips RHS 187A grayed-purple. Lower surface: RHS 138A green.

*Peduncles.*—Length: About 6-25 mm. Diameter: About 1-4 mm. Strength: Strong. Angle: from 45 to 180°. Color: Upper surface: RHS 187A, greyed-purple. Lower surface: RHS 138A, green.

*Pedicels.*—None.

Reproductive organs:

*Androecium.*—Stamen: Quantity: 5, adenate to corolla until pollen has shed. Anther: Shape: Lanceolate, antisepalous, introse, basifixed and two-celled Curling after shedding pollen. Length: About 1 mm, filament 4 mm. Color: RHS 158B, yellow-white. Pollen: Amount: Average. Color: RHS 158B, yellow-white.

*Gynoecium.*—Pistil: Quantity: 1. Length: 20 mm. Stigma: Shape: tripartite. Color: RHS 155D, white. Style: Length: About 2 mm. Color: RHS 155D, white. Ovary: Color: RHS 150D, yellow-green.

Seed/fruit: None observed.

Root: Structure: Fibrous with many rhizomes. Color: RHS 156B, greyed-white.

Weather tolerance: Plants of the new *Campanula* have generally good tolerance to drought, rain and wind, with low temperature resistance to −20° C.

I claim:

1. A new and distinct cultivar of *Campanula* plant named 'PKMTAK3', as illustrated and described herein.

* * * * *